(12) United States Patent
Golay et al.

(10) Patent No.: US 11,391,804 B2
(45) Date of Patent: Jul. 19, 2022

(54) PHANTOM FOR MULTI-PARAMETRIC CALIBRATION IN MAGNETIC RESONANCE IMAGING

(71) Applicant: GOLD STANDARD PHANTOMS LIMITED, London (GB)

(72) Inventors: Xavier Golay, London (GB); Aaron Oliver-Taylor, London (GB)

(73) Assignee: Gold Standard Phantoms Limited, London (GB)

(*) Notice: Subject to any disclaimer, the term of this patent is extended or adjusted under 35 U.S.C. 154(b) by 10 days.

(21) Appl. No.: 17/040,648

(22) PCT Filed: Mar. 25, 2019

(86) PCT No.: PCT/GB2019/050837
§ 371 (c)(1),
(2) Date: Sep. 23, 2020

(87) PCT Pub. No.: WO2019/180464
PCT Pub. Date: Sep. 26, 2019

(65) Prior Publication Data
US 2021/0018584 A1 Jan. 21, 2021

(30) Foreign Application Priority Data
Mar. 23, 2018 (GB) .................................. 1804720

(51) Int. Cl.
*G01R 33/58* (2006.01)
*G01R 33/56* (2006.01)
(Continued)

(52) U.S. Cl.
CPC ......... *G01R 33/58* (2013.01); *G01R 33/5601* (2013.01); *G01R 33/5608* (2013.01); *G01R 33/56341* (2013.01); *A61B 5/055* (2013.01)

(58) Field of Classification Search
USPC ....................................................... 324/309
See application file for complete search history.

(56) References Cited

U.S. PATENT DOCUMENTS 5,034,969 A 7/1991 Ozaki
8,030,922 B2 * 10/2011 Roland .............. G01R 33/4804
324/309

(Continued)

FOREIGN PATENT DOCUMENTS

DE 102016121212 A1 6/2017
WO 2016/138449 A1 9/2016
WO 2017148805 A1 9/2017

OTHER PUBLICATIONS

Kathryn E. Keenan et al: "Quantitative Magnetic Resonance Imaging Phantoms: A Review and the Need for a System Phantom", Quantitative MRI Phantoms Review, Magnetic Resonance in Medicine, vol. 79, No. 1, Oct. 30, 2017 (Oct. 30, 2017), pp. 48-61, XP055494505, US ISSN: 0740-3194, DOI: 10.1002/mrm.26982 cited in the application.

(Continued)

*Primary Examiner* — Rodney E Fuller
(74) *Attorney, Agent, or Firm* — Conley Rose, P.C.

(57) ABSTRACT

A phantom for use in an MRI scanner includes an outer housing and a plurality of vessels located within the outer housing, where each of the vessels contains a material. The value of a property of the material at a particular temperature is different for each of the vessels. The phantom also includes a phase change material between the outer housing and the vessels. Also provided are a method for manufacturing a phantom, a method for obtaining calibrated measurements from non-calibrated images using a phantom, a system for obtaining calibrated measurements from non-calibrated images, and a coil assembly for use in an MRI scanner.

21 Claims, 7 Drawing Sheets

(51) Int. Cl.
*G01R 33/563* (2006.01)
*A61B 5/055* (2006.01)

(56) References Cited

U.S. PATENT DOCUMENTS

| | | | | |
|---|---|---|---|---|
| 9,289,154 | B2* | 3/2016 | Schmidt | G01R 33/4804 |
| 9,603,546 | B2 | 3/2017 | Horkay et al. | |
| 2011/0043206 | A1 | 2/2011 | Kimura et al. | |
| 2015/0323639 | A1 | 11/2015 | Boss | |
| 2016/0363644 | A1 | 12/2016 | Wang | |
| 2017/0184696 | A1 | 6/2017 | Zuccolotto et al. | |
| 2018/0038922 | A1* | 2/2018 | Lu | A61B 8/5261 |
| 2019/0033419 | A1* | 1/2019 | Golay | G01R 33/58 |

OTHER PUBLICATIONS

E. Vescovo et al: "High-Precision Calibration of MRS Thermometry Using Validated Temperature Standards: Effects of Ionic Strength and Protein Content on the Calibration", NMR Biomed., 2013, 26, (2), 213-223, Published online in Wiley Online Library: 2012 (wileyonlinelibrary.com) DOI: 10.1002/nbm.2840.

Kathryn E. Keenan et al: "Design of a Breast Phantom for Quantitative Magnetic Resonance Imaging", J. Magn Reson Imaging, Sep. 2016; 44(3): 610-619, DOI: 10.1002/jmri.25214.

PureTemp 37 Technical Data Sheet, PureTemp LLC; http://www.puretemp.com/stories/about-puretemp-llc.

Keenan et al: "Multi-site, Multi-vendor Comparison of T1 Measurement Using ISMRM/NIST System Phantom", Program #3290; National Institute of Standards and Technology; https://ws680.nist.gov/publication/get_pdf.cfm?pub_id=919826.

International Search Report and Written Opinion dated Sep. 10, 2019 for Application No. PCT/GB2019/050837.

UKIPO Search Report dated Aug. 15, 2018, for Application No. GB1804720.9.

UKIPO Examination Report dated May 22, 2019, for Application No. GB1804720.9.

UKIPO Examination Report dated Oct. 10, 2019, for Application No. GB1804720.9.

UKIPO Examination Report dated Jan. 16, 2020, for Application No. GB1804720.9.

* cited by examiner

PHANTOM FOR MULTI-PARAMETRIC CALIBRATION IN MAGNETIC RESONANCE IMAGING

CROSS-REFERENCE TO RELATED APPLICATIONS

This application is a 35 U.S.C. § 371 national stage application of PCT/GB2019/050837 filed Mar. 25, 2019, and entitled "A Phantom for Multi-Parametric Calibration in Magnetic Resonance Imaging," which claims priority to application No. GB 1804720.9 filed Mar. 23, 2018, both of which are incorporated herein by reference in their entirety for all purposes.

The present invention relates to a phantom, a method for manufacturing a phantom, a method for obtaining calibrated measurements from non-calibrated images using a phantom, a system for obtaining calibrated measurements from non-calibrated images using a phantom, and a coil assembly for use in an MRI scanner.

Magnetic resonance imaging (MRI) is one of the most commonly used imaging techniques for medical diagnosis. As a technique it is of huge value because it provides an imaging method which is non-intrusive and which can provide information about physiological processes occurring in the body (such as fMRI) as well as detailed images of a patient's anatomy. MRI works via the application of strong magnetic fields and radio frequency pulses which affect the behaviour of the intrinsic momentum of protons within hydrogen, and other atoms with odd atomic numbers, in the body. Radio frequency signals are emitted as atoms return to their equilibrium state following the application of a pulse of radiation. The speed at which various properties return to this state allows information to be gleaned about the surrounding material, and magnetic field gradients allow the signal to be spatially resolved.

By varying the scanner settings, a range of different properties of the scanned tissue can be quantified. Particular examples are described below, some of which make use of two or more images taken in succession. Other imaging methods than those described, such as Arterial Spin Labelling and those using T2* weighting, can be used, depending on the tissue property of interest. T2* weighted dynamic contrast enhanced imaging, known as dynamic susceptibility contrast (DSC), can be used in place of or in addition to the T1 weighted imaging described below, for example. Other quantitative imaging techniques can be used for the quantification of water and fat, based on their difference in T1, T2 and/or resonance frequencies.

The spin-lattice relaxation rate, also called T1 relaxation rate, is the most basic contrast in MRI. It represents the time for the induced magnetization to grow to equilibrium once an object is inserted into a magnet, or after an RF selection pulse has been used to produce an image. Importantly, it is also used as the basis of an important procedure to estimate the perfusion parameters into a tissue. In particular, in the case of tumours or tissue with abnormal vasculature, the injection of a T1-shortening contrast agent, such as a contrast agent based on Gadolinium chelates will result in a sharp increase in a T1-weighted image, indicating the presence of abnormal vasculature and increase in blood volume, as well as more rapid extravasion of contrast agent into the tissue. All these aspects can be measured using a method called Dynamic Contrast Enhanced (DCE) MRI, in which a series of T1-weighted images are acquired continuously through the injection of a contrast agent such as a contrast agent based on Gadolinium chelates for example. These T1-weighted images are then combined with a reference quantitative T1 measurement of the tissue to measure the increase in tissue perfusion locally. Quantification of the amount of signal changes can be used to infer the abnormal presence of non-well defined vasculature, characteristic of tumour or other lesions. Quantification of this signal change requires calibration of T1 values in the tissue of interest.

Diffusion weighted imaging (DWI) is a type of magnetic resonance imaging used to produce a map of, among other parameters, an apparent diffusion coefficient (ADC) in different regions. The principle behind diffusion weighted imaging relies on the fact that a reduction in signal due to application of a pulse gradient in the magnetic field can be directly related to the amount of diffusion that is occurring in a particular imaged volume. The main restriction on the diffusion of water molecules within a tissue is due to the presence of intracellular organelles and cell membranes, so that a denser tissue will result in more restricted diffusion than a less dense tissue. This results in a lower ADC in denser areas and is particularly useful in the detection and categorisation of tumours and cerebral infarction. The strength of the signal in a particular voxel of a DWI image allows a person operating the scanner to determine the rate of water diffusion in that region or the flux of water molecules across surfaces of the volume, since the strength of the image signal will be inversely proportional to the rate of diffusion. The ADC represents the mean diffusion within a voxel. In non-isotropic tissue, such as but not limited to the brain, the cardiac tissue, or most muscular or orientated tissues, the diffusion characteristics are anisotropic, as the water diffuses at different rates across the fibres and along the fibres. A simple model of diffusion is therefore represented by e.g. a mathematical object called a tensor. The ADC is in these cases sometimes calculated as the sum or average of the diffusion tensor's diagonal elements (equal to the trace of the tensor) where the diffusion tensor components represent the diffusion rates fitted to a general three-dimensional Gaussian.

Methods such as those described above generally quantify the differences between measured signal properties of the MRI images, such as T1, T2 or T2*, or ADC between two or more images taken in series. A measurement of the ADC, for example, requires two images between which the diffusion gradient is varied. Such parameters are a powerful tool for use in medical diagnosis. Methods for analysing MRI images are becoming increasingly more complex, and now involve the application of machine learning. Radiomics, for example, is a computer-based method for image analyses in which a large number different quantifiable parameters (such as but not limited to the ADC, T1 or T2 relaxation time, and parameters derived therefrom) are determined for each voxel within an image. Patterns within the images can then be analysed algorithmically in order to improve the detection of abnormalities within a scanned region. These methods require accurate measurements of the relevant parameters and rely on the assumption that images are properly calibrated, which is often not the case. As the field of radiomics grows, accurate calibration of the measurements of physical properties derived using MRI will become increasingly more important.

MRI, and in particular multi-parametric magnetic resonance imaging (mpMRI), is useful in the detection of abnormalities in a number of tissues and organs, including the prostrate as well as the brain and other soft tissues, tendons, and ligaments. Although mpMRI can be used to detect abnormalities in a variety of tissues, it has been found to be particularly useful in the diagnosis of prostate cancer, which affects a sixth of all men and remains the most common cancer. In 2013 over 47,000 men were diagnosed with prostate cancer in the UK, with 90% of cancers which are detected early on having no associated symptoms. A high level of prostate specific antigen (PSA) in the blood can be an indicator of prostate cancer, however it can also be as a result of infection or inflammation and so is not a particularly reliable indicator. If a raised level of PSA is detected, a biopsy will usually be recommended. This is an intrusive and uncomfortable procedure for the patient. A biopsy also requires the administration of an anaesthetic and can still result in a false negative since large regions of the prostate may be missed.

Only fairly recently has it been possible to diagnose prostate cancer using magnetic resonance imaging techniques. Multi-parametric MRI (which quantitative methods may include diffusion weighted imaging and dynamic contrast enhanced imaging based on the shortening of T1 through the passage of a T1-shortening contrast agent, such as a contrast agent based on chelated Gadolinium) can both localise a tumour and estimate Gleason grade representing the aggressiveness of the cancer, making it a useful supplement to, or replacement for, tissue biopsy. The use of MRI in prostate cancer diagnosis is soon to be implemented in revised NICE guidelines. This technique, however, is still not perfect (around 10 percent of patients with mpMRI negative are underdiagnosed and around 25 percent with mpMRI positive are overdiagnosed). More recently, scientists have been working on the use of machine learning to improve the stratification of patients using mpMRI techniques. These methods require quantitative measurements of the signal within both quantitative T1 and Diffusion images in order to be able to effectively compare scans between patients. This may be possible in a single location using a single scanner, but it cannot at present be rolled-out across multiple centres due to the lack of consistency between measurements taken using different scanners.

Although imaging methods, such as DWI, T1, T2, T2*, and arterial spin labelling (ASL) are constantly improving as the capability of the scanners used increases, there is still no consistent way to quantify the parameters measured using these methods. In addition, many measurable parameters including the ADC in particular, and T1 and T2/T2* to a lesser extent, are highly dependent on temperature (since clearly motion of the water molecules will be affected by an increase or decrease in temperature, which will affect both diffusion values and potential for relaxation of the signal through the lattice or spin-spin interactions). Accounting for this can be complex and inaccurate. What is required is an effective way to calibrate MRI scanners for these imaging methods in order to achieve consistency across multiple centres, which will enable the widespread use of quantitative mpMRI to provide precise active surveillance metrics, reduce the percentage of equivocal diagnosis (which may lead to invasive interventions such as biopsy), and reduce the occurrence of under or overdiagnosis. The above benefits will help to reduce associated healthcare costs, conserving valuable funding.

Phantoms for use in an MRI scanner are known. DE-A-10 2016 121 212 (HA Imaging GmbH) describes a phantom for deriving the spatial and ADC resolution in diffusion weighted images. The phantom comprises a cylindrical body including different compartments filled with PVP solution or another thickening agent at different concentrations. Since the ADC values of the liquids used are highly temperature sensitive, the phantom can include a thermometer to measure the temperature of the fluid. The ADC value can then be corrected to a reference temperature using calibration curves.

High Precision Devices, Inc. advertises a phantom for quantitative MRI diffusion imaging which comprises a plastic sphere containing a number of vials each filled with an aqueous solution of PVP (polyvinyl pyrrolidone) at different concentrations. The vials are held at 0° C. during a scan of the phantom using an ice-bath.

US-A-2017/0184696 again describes a phantom for calibration of diffusion weighted images taken using an MRI scanner and used to calibrate images which track the brain's fiber network. The phantom comprises a series of hollow tubular polymer fibers filled with a fluid. The phantom is maintained at a constant temperature by way of a temperature controlling fluid which is cycled through conduits next to an inner shell of the device.

The National Institute of Child Health and Human Development (the NICHD) has developed a diffusion phantom, described in U.S. Pat. No. 9,603,546, which takes the form of a hollow sphere containing PVP. The PVP is chosen so that it has an ADC value similar to that of human tissue. The phantom includes a chamber containing an aqueous solution including polymers with different molecular weights. The relative proportion of the polymers in solution can be varied to adjust the diffusive properties of the phantom. In an embodiment, the phantom may include two separate chambers and a central reference compartment containing a saline solution which has an ADC very different from that of the solutions in the two surrounding compartments. It is not clear from the description whether the two compartments contain solutions having a different concentration relative to one another, or what substances make up these solutions. A thermometer is provided on the outside of the sphere.

The article entitled "High-precision calibration of MRS thermometry using validated temperature standards: effects of ionic strength and protein content on the calibration" (Vescovo et al; NMR Biomed., 2013, 26, (2), 213-223) describes use of a material at a stable temperature to measure the effect of tissue material on temperature using magnetic resonance spectroscopic thermometry.

The National Institute of Standards and Technology (NIST) has developed a phantom for standardisation of T1 and T2 images taken of the head using an MRI machine. The phantom contains a number of spheres housed within a larger spherical housing. The same institute has produced a phantom for calibration of MRI imaging of ADC within breast tissue using ports filled with varying concentrations of PVP (this phantom is described in "Design of a Breast Phantom for Quantitative MRI"; Keenan et al; J. Magn. Reson. Imaging 2016).

At present, there are no phantoms providing an accurate measure across a range of measurable values (such as ADC and combined ADC and T1 values) and most are too cumbersome to cool to the required temperature easily (usually 0° C.). In addition, there are no such phantoms existing, in particular for Diffusion or Diffusion and T1/T2/T2* imaging over a range of values, which can be imaged along with a patient. In the case of ADC phantoms, for example, current models, based on diffusion values present at 0° C., cover a range of ADC values which represent cancerous (denser) tissues but not normal tissue and the dependence of the ADC values on temperature means that corrections for changes in temperature need to be made which complicates the process. Similarly, non-linearity in measurements presents a problem since there is at present no reliable way to correct for this. There is a need for an improved phantom for the calibration of MRI images which is able to provide an accurate in-image calibration system.

According to a first aspect of the present invention, there is provided a phantom for use in an MRI scanner comprising: an outer housing; a plurality of vessels located within the outer housing, each of the vessels containing a material, wherein the value of at least one property of the material at a particular temperature is different for the material contained within each of the vessels; and a phase change material between the outer housing and the vessels.

The particular combination of a series of vials containing liquids having different and known values for a property which is measurable (quantifiable) using MRI scanner, such as the diffusion coefficient and/or T1 or T2 relaxation time, and a phase change material which is able to maintain the material within the vessels at a constant temperature during a scan means that the value of the relevant physical property of the liquid in each of the vessels can be properly controlled (even given the sensitivity of properties such as the diffusion coefficient to changes in temperature) without the need to apply corrections to account for changes in temperature during the scan. The phantom can also be maintained at a precise temperature, which is comfortable for a patient who may be in contact with the phantom during the scan and this can be done without the need for bulky equipment or the use of a separate heating system, be it through the addition of electrical components or fluid exchange compartments. The term outer housing refers to the fact that the housing is located outward of the vessels. The outer housing may or may not be the outermost housing of the phantom. Two or more images may be required to determine a value of particular parameters (such as the ADC which requires a comparison of two images taken at different times). The examples provided below refer to vials, however any type of vessel can be used in place of these vials provided that the vessel is capable of containing the material within when the phantom is in use.

These features allow for use of the phantom as an in-image calibration device. In-image refers to the fact that the phantom and subject are imaged at the same time in the same scanner. The raw image data may then contain images of both the phantom and the subject next to one another. The diffusion coefficient in particular is also dependent on pressure and measures are usually given for materials in their standard state (at 25° C. and 100 kPa). The materials in each of the vessels will therefore have different diffusion coefficients and/or different values of the relevant property in their standard state. The vessels may be of any shape, provided that they are able to contain the material (which may be a liquid) in use.

Of course, for use with in multi-parametric imaging methods, several properties may be determined during a scan or during a series of scans and it may be advantageous for a single phantom to be able to calibrate images taken using several different imaging methods. The material or liquid within the vessels may therefore be chosen to provide a useful range in two or more different measurable properties for calibration purposes. Alternatively, the vessels can be easily replaceable or refillable (as described in more detail below) in order that the liquid used for calibration can be changed to optimise the phantom for the calibration of an image taken using a particular imaging method. A phantom can also be configured to contain two or more sets of vials containing different materials, where each set can be used for calibrating a particular measurement.

The phantom may be designed as an in-image phantom and should in such a case be adapted to fit within the bore of the scanner along with a patient or the body part of a patient of which an image is being taken. Any suitable shape can be used for the phantom, however shapes which provide a comfortable fit to the body part of the patient to be scanned, and shapes which can fit within or attach to the coils of the scanner, are particularly advantageous.

In embodiments, at least a part of the outward facing surface of the outer housing is a concave surface. Because the phantom is designed as an in-image phantom, and because of the long scan times required to produce a diffusion weighted image as well as a DCE (Dynamic Contrast Enhancement) examination, it is important to ensure that the patient is comfortable when inside the scanner. The closer the phantom can be located to the body part to be imaged the better because of possible spatial variations within the scanner. The convex outer surface of the phantom will fit comfortably around the trunk of a patient (either placed on the stomach or underneath the back). Outward facing refers to the fact that the surface faces generally away from the rest of the phantom or from the vessels located within the phantom. FIGS. 2A and 2B, for example, illustrate a housing having outward facing concave surface and an outward facing convex surface parallel to this.

In embodiments, the vessels are each fixed at an equal distance from the concave surface. When the patient lies on top of the phantom or the phantom is placed on top of the patient inside the scanner, the vessels are then equidistant from and close to the body part to be imaged, helping to improve consistency and accuracy of the calibration.

In embodiments, the outer housing comprises a convex outward facing surface parallel to the concave surface and the vessels are fixed in place between the convex and concave surfaces. This configuration minimises the amount of material required and the weight of the phantom (important if a patient is to be located underneath the phantom during a scan).

In embodiments, the outer housing comprises two flat side faces and the vials extend between and are coupled to the side faces to hold the vessels in position. This again minimises the amount of additional material required to hold the vessels in place and provides a convenient location for openings for filling or refilling the vessels.

In embodiments, the outer housing is shaped as a cuboid. The housing may be cube-shaped in embodiments. In both cases the structure of the outer housing is simple to manufacture. The cuboid housing may be generally shaped as a cuboid but may have cut-away portions, for example at the corners as shown in FIG. 4. In embodiments, the outer housing has a maximum dimension of between 5 cm and 25 cm. The maximum dimension refers to the longest measurement that can be taken across the housing volume. Sizing the housing in this way makes it possible to fit the phantom within voids or gaps between coils of the scanner. A phantom shaped as a cube provides a convenient shape to achieve this. Vessels can extend across the phantom between two parallel faces of the cube and can then be easily accessed if plugs in the outer housing are used. A housing which is cuboid in shape is based on three pairs of generally parallel flat surfaces, which are small enough to be integrated in a receiver coil positioned close to the body of the patient. In embodiment, the phantom can be positioned within a flexible surface coil to be used for example on the abdomen or in the back of a patient lying supine in the scanner. In embodiment, the phantom can be positioned within a hard surface coil for the patient to lie on, prone or supine, which can be integrated into the patient table.

In embodiments, the outer housing is configured to be positioned adjacent the inner surface of an RF coil used within the scanner. This is particularly useful in the case of a head, neck, or head and neck coil. In embodiments, the outer housing is ring-shaped. The ring is hollow to contain the vessels, which vessels can be spaced equidistantly within the ring, although this is not required. This ring can be sized to fit within an RF coil of the scanner adjacent the inner surface of the coil or can be integrated with the coil. A clip or other attachment mechanism may also be used to hold the phantom in place or it may simply sit within the coil in use. The phantom may be removable from the coil.

In embodiments, the plurality of vessels comprises at least 3 vessels. In embodiments, the plurality of vessels comprises 8 to 12 vessels. The phantom therefore includes a number of vessels, which may be limited to 3 at the minimum. The maximum number of vessels is not limited, apart from due to the space available. Use of three or more vessels containing different materials allows corrections for non-linearity to be made, as detailed below.

In embodiments, the vessels are vials.

In embodiments, the material within the vessels is a liquid. In embodiments, the liquid within the vessels comprises a material dissolved in a liquid, and the concentration of the material in solution is different for each of the vessels. In embodiments, the liquid within the vials comprises a polymer dissolved in water, and the concentration of the polymer in solution is different for each of the vials. The ADC of the liquid can be easily controlled in this manner and can be made to cover a useful range of values (including both healthy and unhealthy/abnormal tissue). This is a straightforward way to precisely control the value of a particular physical property of the liquid. For example, the diffusion coefficient can be controlled simply by adding a particular amount of a polymer, such as polyvinyl pyrrolidone (PVP) or glycerol, to solution to fix the concentration of the polymer to a desired value. A major issue with the accuracy of calibration methods at present is the inability to account for non-linearity in measurements taken of different properties. In order to account for this non-linearity in calibration, base measurements of a range of values are required for comparison and including three or more vials containing different solutions allows for this.

In embodiments, the polymer is polyvinyl pyrrolidone. PVP is cheap as well as being readily available in controlled formulations, and can be used easily as a material having a controlled apparent diffusion coefficient which can be different for each of the vials simply by varying the concentration of PVP in solution.

In embodiments, the thickening agent can be another polymer or other molecules with higher densities than water. Any water-soluble polymer (cross-linked or not) can be used as the diffusion inducing agent. In embodiments, the molecules can be polyGlycan or Polyglucan molecules based on original glucans or glycans, such as, but not limited to the following:

dextran, α-1,6-glucan with α-1,3-branches
floridean starch, α-1,4- and α-1,6-glucan
glycogen, α-1,4- and α-1,6-glucan
pullulan, α-1,4- and α-1,6-glucan
starch, a mixture of amylose and amylopectin, both α-1,4- and α-1,6-glucans
cellulose, β-1,4-glucan
chrysolaminarin, β-1,3-glucan
curdlan, β-1,3-glucan
laminarin, β-1,3- and β-1,6-glucan
lentinan, a strictly purified β-1,6:β-1,3-glucan from *Lentinus edodes*
lichenin, β-1,3- and β-1,4-glucan
oat beta-glucan, β-1,3- and β-1,4-glucan
pleuran, β-1,3- and β-1,6-glucan isolated from *Pleurotus ostreatus*
zymosan, β-1,3-glucan.

In embodiments, the liquid within the vessels comprises a metallic salt dissolved in water, and the concentration of the metallic salt in solution is different for each of the vessels. A metallic salt solution is useful for providing a range of liquids having different values of the T1, T2, or T2* relaxation time (i.e., for the calibration of images taken using dynamic contrast enhanced imaging methods).

In embodiments, the metallic salt comprises one or more of Nickel Chloride, Copper Sulphate, Gadolinium, Manganese Chloride, and Iron Oxide. Nickel Chloride, Copper Sulphate, and Gadolinium are particularly useful when the phantom is intended to be used to calibrate T1 images. Manganese Chloride is particularly useful in the calibration of T2 images, and Iron Oxide should preferably be used when calibrating T2* images.

In embodiments, the liquid within the vessels comprises a mixture of water and different organic oils.

In embodiments, the phase change material is ethylene carbonate. Ethylene carbonate is colourless, and freezes at a temperature of 36.3° C. which is similar to a patient's skin temperature meaning that the phantom will not cause discomfort when in contact with a patient during the scan. Other phase change materials can be used, as discussed in further detail below.

In embodiments, the phase change material is diphenyl ether. The melting point of diphenyl ether is around 26° C. which again will be comfortable for a patient contacting the phantom. The crystallisation process, as for ethylene carbonate, will proceed for long enough to last at least the average time required for a scan.

In embodiments, the vessels each comprise a vessel inner shell and a vessel outer shell and the phase change material is contained between the vessel inner shell and the vessel outer shell of each of the vessels. This configuration requires less of the phase change material and ensures that the phase change material is located within the phantom as close as possible to the liquid within the vessels, which must be kept at as near to a constant temperature as possible during a scan.

In embodiments, the phase change material fills the whole of the space between the vessels and the outer housing. This configuration is simple and again ensures that the entire outer surface of the vessels contacts the phase change material.

In an embodiment, the outer housing comprises a pluggable opening for filling the phantom with the phase change material. This way the housing of the phantom can be reused and a degree of flexibility is provided in terms of the phase change material used. Different phase change materials have different melting points so that some may be more suitable in certain situations that others.

In an embodiment, each of the vessels comprises a pluggable opening for filling each vessel with the liquid. As for the phase change material, it is useful to be able to empty and refill the vessels in order to adapt the properties of the liquid therein to different situations. A different range of values of the physical property to be measured may be more suitable in scans of certain regions of the body, for example. This ensures that the range of values covers both healthy and unhealthy tissue types as intended.

In an embodiment, the pluggable opening for filling each of the vessels with the liquid is an opening in the outer housing. The outer housing does not therefore need to be opened up and possibly damaged in order to access the vessels for refilling.

In embodiments, the phantom comprises an item of clothing including attachment means, wherein the housing is coupled to the clothing using the attachment means.

In embodiments, the item of clothing is a vest and the attachment means comprises a pocket into which the housing can be placed.

In embodiments, the material within the vessels comprises an injectable MRI contrast agent and the concentration of the contrast agent in each of the vessels is different.

In embodiments, the contrast agent is gadolinium-based.

In embodiments, the material within the vessels comprises a gelling agent.

In embodiments, the material within the vessels comprises a compound with paramagnetic ions.

In embodiments, the ratio of gelling agent to paramagnetic ions is selected such that the material within the vessels matches the intrinsic T1 to T2 ratio of tissue.

According to a second embodiment of the present invention, there is provided a method for manufacturing a phantom for use in an MRI scanner, the method comprising: filling a plurality of vessels with a material, wherein the value of a property of the material at a particular temperature is different for each of the vessels; providing an outer housing surrounding the vessels; and providing a phase change material in the volume between the vessels and the outer housing.

According to a third aspect of the present invention, there is provided a method for obtaining calibrated measurements from non-calibrated images using a phantom, the method comprising: heating the phantom described above to melt the phase change material; allowing the phase change material to cool; disturbing the phase change material to begin a process of crystallisation; locating the phantom within the scanner adjacent a subject to be imaged; scanning the phantom and the subject simultaneously to produce raw image data while the crystallisation process is ongoing; deriving a correction function from values of the property measured from the raw image data of each of the vessels and known values of the property for the material within each of the vessels; and applying the correction function to the image data of the subject to produce a calibrated image.

The phantom may be cooled in the cooling step to around, at or below the freezing temperature of the phase change material. This could be a fraction of a degree below the freezing point, or greater than 10 degrees. The phase change material will become supercooled and will not freeze spontaneously unless disturbed. Only if it is left for a long period of time (hours) will it spontaneously begin freezing.

According to a fourth aspect of the present invention, there is provided a system for obtaining calibrated measurements from non-calibrated images using a phantom, the system comprising; a phantom as described above configured to be imaged in an MRI scanner simultaneously with a subject; and a processor coupled to the phantom and to the scanner for receiving raw image data of the subject and phantom, deriving a correction function from values of the property measured from the raw image data of each of the vials and known values of the property for the material within each of the vessels, and applying the correction function to the image data of the subject to produce a calibrated image.

In embodiments, the system comprises a storage medium for storing the raw and calibrated image data and information about the correction function.

According to a fifth aspect of the present invention, there is provided a coil assembly for use in an MRI scanner, the assembly comprising a radio frequency coil array and a housing, wherein the housing has one or more spaces between the coils and at least one of the spaces contains a phantom as described above.

In embodiments, the housing having a plurality of spaces, wherein two or more of the spaces contain a phantom as described above. The assembly is therefore highly configurable. Another embodiment, wherein the housing of the coil assembly also forms the outer housing of a phantom, is described below with reference to FIG. 3.

Embodiments of the present invention will now be described in detail with reference to the accompanying drawings, in which.

The calibration phantom described below is specifically designed to be imaged at the same time as a patient in the same scanner (as an in-image calibration device). Features of the device, such as the particular shape of the phantom and the proximity of the vials to the outer housing, make this easier and more comfortable for the patient, and improve accuracy of the subsequent calibration stage. This high level of accuracy is achievable using an in-image phantom because changes occurring in the imaging system before or after an image of the subject is taken will not affect the calibration process. Most phantoms are overly bulky and are shaped as a cylinder or sphere preventing them from fitting comfortably within the MRI coil along with the patient or body part to be imaged, so that it is not possible to image the phantom simultaneously with a patient. The system also provides calibration images of material having a range of carefully controlled values of a property to be measured, the range corresponding to values expected to be measured from both healthy and abnormal tissues. Providing a range of measurements for use in calibration can help to correct for non-linearity and ensure that values of the relevant property or properties are measured consistently across images taken at different times by the same scanner and across different scanners.

Figure 1A:
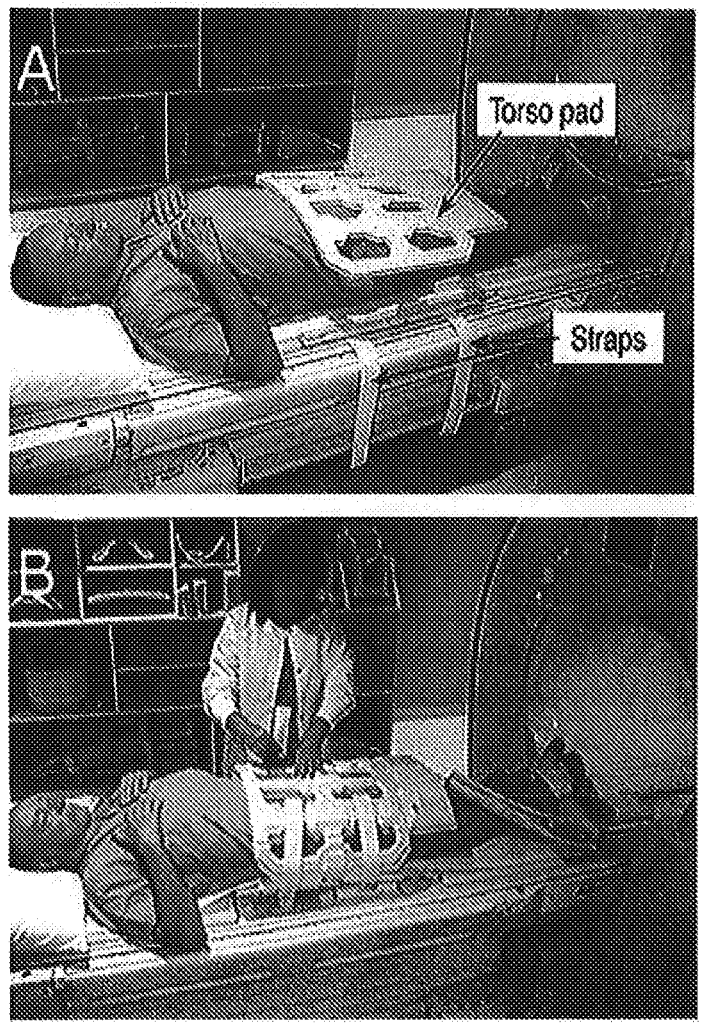
FIG. 1A shows a diffusion phantom located adjacent a patient on a table prior to a scan.
Figure 1B:
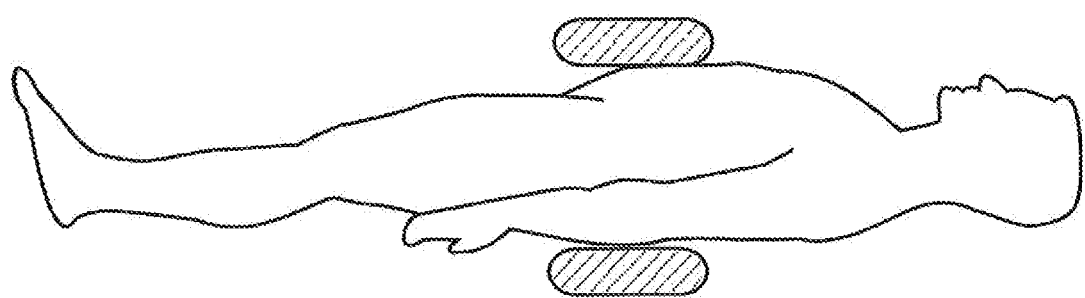
FIG. 1B illustrates a possible location of the phantom housing relative to the patient.

In FIG. 1A, the phantom is located above the body as part of a torso pad and is strapped to the patient's waist to prevent movement relative to the body during scanning. The housing may be waterproof and designed to contain a phase change material which is used to keep vials 4a-k at a constant temperature during the scan, as described in more detail below. The phantom may also be located underneath the patient's torso. FIG. 1B shows a side view of the patient with the torso pad including the phantom strapped around the patient's middle. This may represent a single pad extending all of the way around the body or two separate pads, one strapped above the body and another positioned underneath the lower back of the patient (and possibly integrated into a table on which the patient can lie during a scan).

Figure 2A:
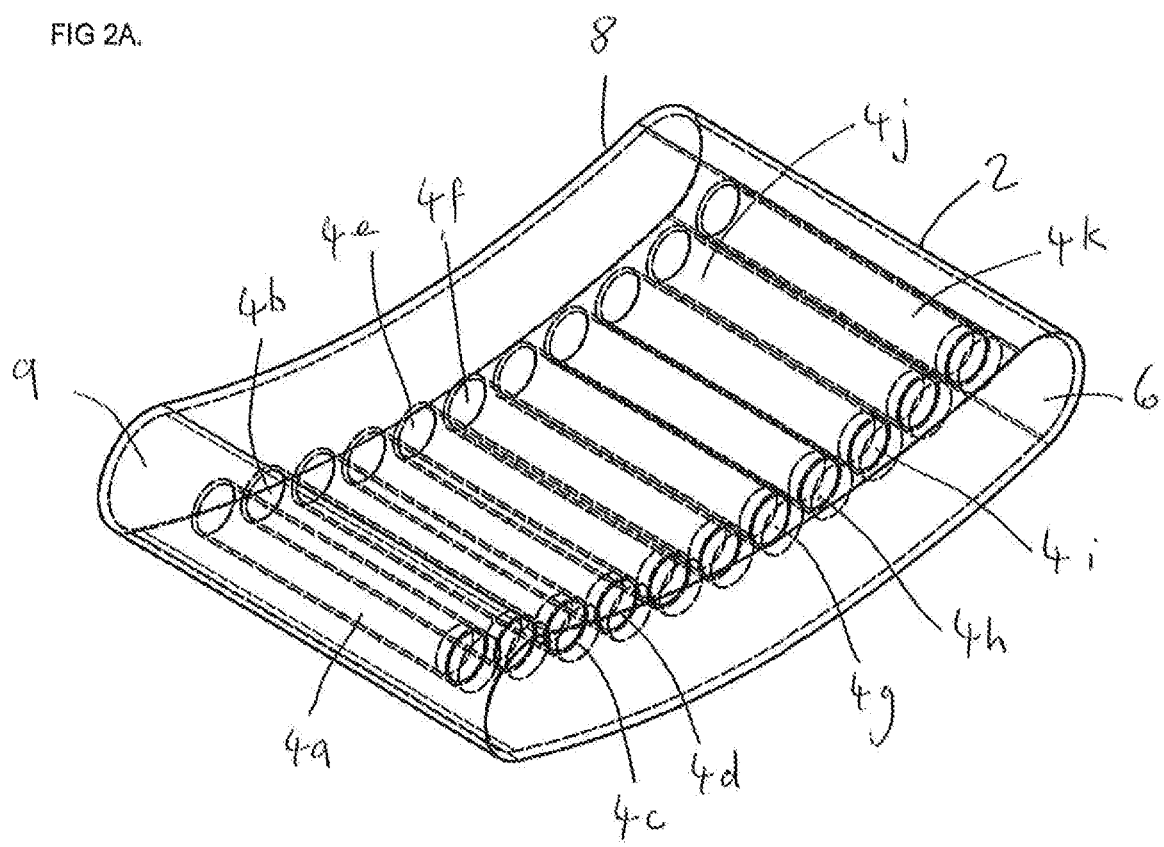
FIG. 2A shows a perspective view of a diffusion phantom.

An example of a phantom is shown in FIG. 2A. The phantom comprises an outer housing or container 2 which is shaped to fit the contours of a patient's body. Within the housing a plurality of vials 4a-k are located, separated from the housing and each containing an aqueous solution, wherein each solution has a different value of a measurable property, such as the apparent diffusion coefficient, T1, or T2 relaxation time (the solution in vial 4a will have a value for the relevant property that is different from that of the solution in vial 4k). The value of the property for each solution may be controlled by adapting the concentration of a particular material in solution. The material may be a polymer such as PVP, useful for providing controlled values of the ADC, or may be a metallic salt or a mixture of different metallic salts, useful for providing controlled values of the T1 or T2 relaxation time. Materials may be dissolved in water to form the solution.

Instead of using chemicals and/or salts to adapt the T1 or T2 relaxation time for the solution contained within the vials, vials can be filled with a contrast agent such as a Gd-based contrast agent which may be mixed with a gel. A different concentration of the contrast agent within the gel can be used for each vial (in a similar way to the varying concentration of PVP in water for the PVP based embodiments). Once the phantom has been imaged adjacent the part of the body for which a measurement is desired, the concentration of the contrast agent within the body can be determined by comparison with images of the vials including substances having known concentration of the same chemical. The vessels in this embodiment may contain water, an injectable MRI contrast agent (such as gadolinium as mentioned above), a gelling agent, and other compounds with paramagnetic ions. Examples of gadolinium-based contrast agents which are suitable for use as a component of the material within the vessels are Magnevist® and Dotarem®. Suitable gelling agents include agar, agarose, gelatin, sodium alginate, hydroxyethylcellulose, poly-acrylic acid (carbomer and carbopol), and polyacrylamide. Suitable compounds with paramagnetic ions include nickel chloride, manganese chloride, nickel nitrate, and copper sulphate.

An example solution contains between around 0.1 mM and 4.0 mM of nickel chloride, between 0.01 mM and 0.1 mM of manganese chloride, between 0.25% and 3% of one of hydroxyethylcellulose, carbomer, or polyacrylamide, and between 0.01% and 1% of Magnevist®. The remainder of the solution may be made up from water. Mixtures of hydroxyethylcellulose, carbomer, or polyacrylamide wherein the total amount is between 0.01% and 1% may also be used. The precise amounts of the components used will depend on magnetic field strength.

Some concentrations of nickel chloride in solution with water within a phantom required to provide particular relaxation rates can be found in Table 1 below, which is from the paper entitled "Quantitative Magnetic Resonance Imaging Phantoms: A Review and the Need for a System Phantom" by Keenan et al. (MRM, 2018, January 79(1):48-61).

TABLE 1

Theoretical Sphere $R_1$ (=$1/T_1$) Values at 3 T and Corresponding $NiCl_2$ Concentration

| Sphere | VIF spheres | | Tissue spheres | |
|---|---|---|---|---|
| | $R_1$ ($s^{-1}$) | $[NiCl_2]$ (mg/L) | $R_1$ ($s^{-1}$) | $[NiCl_2]$ (mg/L) |
| 1 | 0.75 | 87.1 | 0.67 | 69.68 |
| 2 | 2.63 | 479.03 | 0.94 | 127.40 |
| 3 | 6.56 | 1302.09 | 1.33 | 209.03 |
| 4 | 11.56 | 2347.24 | 1.89 | 324.48 |
| 5 | 17.56 | 3601.42 | 2.67 | 487.74 |
| 6 | 24.56 | 5064.64 | 3.77 | 718.69 |
| 7 | 32.56 | 3736.68 | 5.33 | 1045.15 |
| 8 | 41.56 | 8616.16 | 7.54 | 1506.93 |

Note:
The $R_1$ values were chosen to mimic the range of values typically encountered in a DCE-MRI study for both the VIF and tissue compartments. To achieve these relaxation rates, the corresponding concentrations of $NiCl_2$ are provided, assuming a water-relaxation rate of 0.33 $s^{-1}$ and $NiCl_2$ relaxivity of 0.62 (mM · s)$^{-1}$ at 3T.

The ratio of the gelling agent to paramagnetic ions is preferably selected such that the T1 to T2 ratio of the material within the vessels corresponds to that of human tissue (e.g. 300-3000 ms and 10-250 ms respectively). The vessels are maintained at a temperature near to body temperature (such as at 37° C.) by the phase change material such that an image of the vessels containing different concentrations of contrast agent can be directly compared the image of the subject. This then permits direct linearisation of the MRI signal to the concentration of the contrast agent (or calibration of the image signal using the images of the material within the vessels).

Clearly, it is still important for the vials and the substances contained within to be held at a temperature that is as close to body temperature as possible for comparison with a particular body part. Phase change materials may be used in order to achieve this and the structure of the housing and vials may be identical to that used in embodiments where vials contain PVP or another water-soluble material. Determination of the concentration of a contrast agent in a body part of the patient does not require analysis of T1 or T2 relaxation time, which can result in simpler and quicker image processing.

Vials are preferably held in place relative to the outer housing during use. This may be by way of one or more struts per vial which can be formed of the same material as the housing and which extend from the vial to the outer housing. Alternatively, the vials themselves may extend all the way through the phantom from one side 6 of the outer housing to the other side 8 (although they must, of course, themselves be watertight in order to ensure that the solution within the vials does not leak out). In embodiments, the outer housing 2 and vials 4 can be formed of the same material and may be formed as one piece in order to simplify the manufacturing process.

The housing and/or the vials can be of a variety of different shapes and may be formed by injection moulding, vacuum forming, blow moulding, casting, machined from solid blocks, or may be formed from sections of plate glued, welded or held together with fasteners. These may be formed together as a single piece or separately. Alternatively, but less advantageously, the housing could be made from glass, which would be blown into shape. A suitable material to use to form the housing and/or vials is plastic, however if ethylene carbonate (which is a solvent) is used as the phase change material the plastic of the housing and vials will need to be chemically resistant. Plastics such as polyethylene, polypropylene, Nylon, Polyamide, Polyether ether ketone (PEEK), Polyvinylidene fluoride, and fluoropolymers are particularly useful in this case as they are not dissolved by the ethylene carbonate. Any other plastic which will not be dissolved in contact with the phase change material will also be suitable. In an embodiment, the housing and/or vials can be protected from the phase change material, for example using an internal/external layer or coating of a different material. Once the housing is formed, the phase change material may be poured in through a pluggable opening, ensuring that no contaminants are introduced.

Once the vials and the outer housing are formed, these can be filled with at least the solutions and phase change material respectively through openings which are then closed off to form watertight chambers to prevent mixing of the different components. Openings may be provided with a removable closure mechanism (a plug, for example) so that the phase change material and the solutions within the vials can be replaced if necessary. This way there is some flexibility in the type of phase change material used and the concentration or make-up of the different aqueous solutions contained within the vials. In particular, it is advantageous in all cases (particularly where a phantom is intended to be imaged with the subject as an in-image phantom) to use a phase change material which has a transition temperature (or melting point) close to body temperature, so in the range between 25° C. to 45° C., preferably between 36° C. and 38° C., preferably between 36.5° C. and 37.5° C., and preferably around 37° C. This means that during crystalisation the material in the vessels and the phase change material will be maintained at around body temperature. The phantom can be comfortably held close to the body part to be imaged and the conditions within the vessels will be similar to that within the body, which can make the calibration process more accurate).

The vials 4 may each contain an aqueous solution comprising PVP (polyvinyl pyrrolidone), which is a water soluble polymer, or another thickening agent. When dissolved in water the ADC of the water plus PVP/thickening agent solution (at a particular temperature and pressure) depends on the concentration of agent present. Vials can be of any shape, but are preferably cylindrical as shown in FIG. 2A. The concentration of PVP/thickening agent within the aqueous solution is different for each of the vials such that the different solutions cover a range in PVP/thickening agent concentration which is designed to mimic the range of measured ADC values in the human body at room temperature. Table 1 lists various concentrations of PVP in aqueous solution along with the associated ADC of the solution. Values are given at 36.3° C., which is the fixed point temperature of ethylene carbonate. Measured ADC values for different concentrations of PVP can be sourced from https://www.ncbi.nlm.nih.gov/pubmed/28628638, and ADC values for benign and malignant tissue values can be found at https://www.ncbi.nlm.nih.gov/pmc/articles/PMC4632135/.

TABLE 1

| PVP Conc (% w/w) | ADC ($\mu m^2/ms$) |
|---|---|
| 0 | 3.05 |
| 10 | 2.49 |
| 20 | 1.88 |
| 30 | 1.36 |
| 40 | 0.90 |
| 50 | 0.57 |

The vials 4 may each contain an aqueous solution comprising water combined with metallic salts such as Nickel Chloride, Copper Sulphate, Gadolinium, Manganese Chloride, and Iron Oxide. When dissolved in water, the T1 of the water plus a variable concentration of metallic salts (at a particular temperature and pressure) depends on the concentration of the salts present. Vials can be of any shape, but are preferably cylindrical as shown in FIG. 2A. The concentration of salts within the aqueous solution is different for each of the vials such that the different solutions cover a range in salt concentration which is designed to mimic the range of measured T1 values in the human body at room temperature. Table 2, which is sourced from https://ws680.nist.gov/publication/get_pdf.cfm?pub_id=919826, lists example values of the concentration of aqueous nickel chloride and associated T1 measurements at 3 T.

TABLE 2

| $NiCl_2$ Conc (Mm) | T1 (ms) |
|---|---|
| 0.299 | 1989 |
| 0.623 | 1454 |
| 1.072 | 984.1 |
| 1.720 | 706 |
| 2.617 | 496.7 |
| 3.912 | 351.5 |
| 5.731 | 247.13 |
| 8.297 | 175.3 |
| 11.936 | 125.9 |
| 17.070 | 89.0 |
| 24.326 | 62.7 |
| 34.590 | 44.53 |
| 49.122 | 30.84 |
| 69.680 | 21.719 |

Figure 2B:
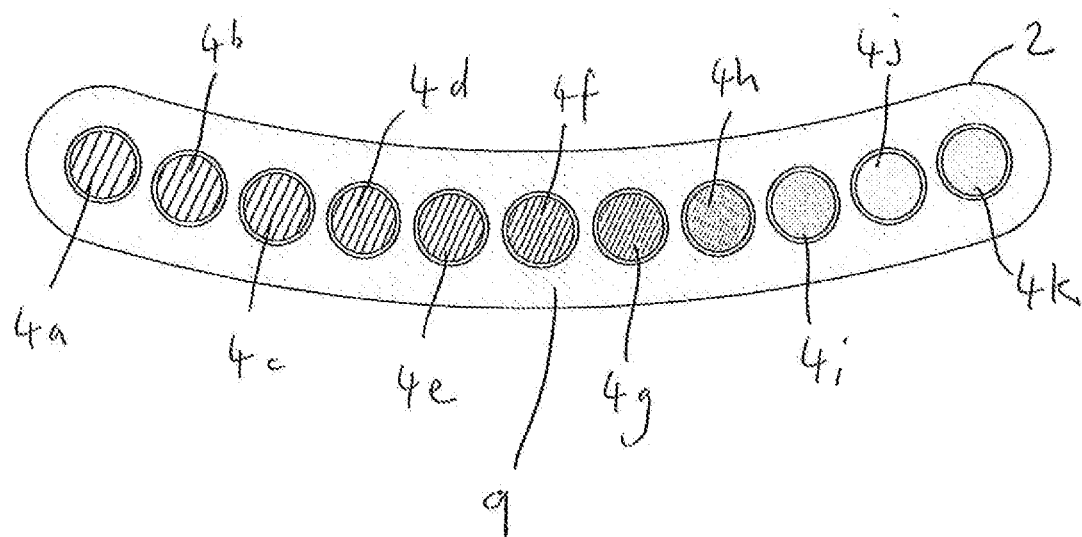
FIG. 2B shows a side view of the diffusion phantom shown in FIG. 2A with vials shaded to represent the concentration of PVP in the solution within each vial.

FIG. 2B shows a side view of the diffusion phantom of FIG. 2A. The curved shape of the outer housing 2 is visible and the ends of the vials are shown, shaded to represent the concentration solution in the liquid contained in each of the vials. Of course, the actual appearance of the solution may not be different and the shading is used in order to illustrate the change in concentration and the fact that, in this example, concentration of PVP or thickening agent, metallic salt, or another material increases from one end of the phantom to the other as described below. The major surfaces of the phantom housing can be straight rather than curved, or the phantom can be shaped to fit to or within coils as described further below. If the phantom is designed to be used to image the torso, the shape could be made to correspond to the average curvature of the lower back of a sample of people (or a sample of a particular subset of people, such as those in a particular age range, gender, or gender and age range).

The device shown in FIGS. 2A and 2B comprises 11 vials, however more or fewer vials may be provided to allow for a simpler structure, or for a more accurate calibration, for example two vials at different concentration can be provided, or more than 11 vials can be provided. Generally, the number of vials present will be in the range 3 to 15, preferably 8 to 12 in order to cover a range that is large enough to cover healthy and abnormal tissue at high enough resolution to provide accurate calibration. The vial closest to one end of the phantom may contain a solution having the lowest concentration and the vial closest to the other end of the phantom may contain a solution having the highest concentration (as shown in FIG. 2B). If this is the case, vial 4a in FIG. 2B will contain the weakest solution and vial 4k will contain the strongest solution. Vials in between will contain solutions having intermediate concentrations. Concentrations may be increased between adjacent vials by equal increments in percentage by mass concentration in the solution. Non-linear increments in concentration may also be useful in some circumstances. Logarithmic or exponential increments could be used, for example. T1, T2, and ADC decay (among others) are generally represented by an exponential decay. This means that by using logarithmic-based increments in concentration of material within the vials, a linear change in signal strength between images of the various vials can be achieved. This is more straightforward to deal with in terms of processing.

For T1 calibration, for example, the vial closest to one end of the phantom may contain a solution having the lowest concentration of metallic salts and the vial closest to the other end of the phantom may contain a solution having the highest concentration of metallic salts (as shown in FIG. 2B). If this is the case, vial 4a in FIG. 2B will contain the weakest solution and vial 4k will contain the strongest solution. Vials in between will contain solutions having intermediate concentrations of salts. Concentrations may be increased between adjacent vials by equal increments, logarithmic increments, or other increments in percentage by mass concentration of salt in the solution. For ADC calibration the above will still apply, however PVP may be used as the material in solution rather than or as well as metallic salts. Additional substances, such as a preservative and trace quantities of paramagnetic metal to optimise MR relaxation properties, may be used as additives in the solution. Vials may also be spaced physically along the phantom in an equidistant manner (with an equal spacing between adjacent vials).

Figure 3:
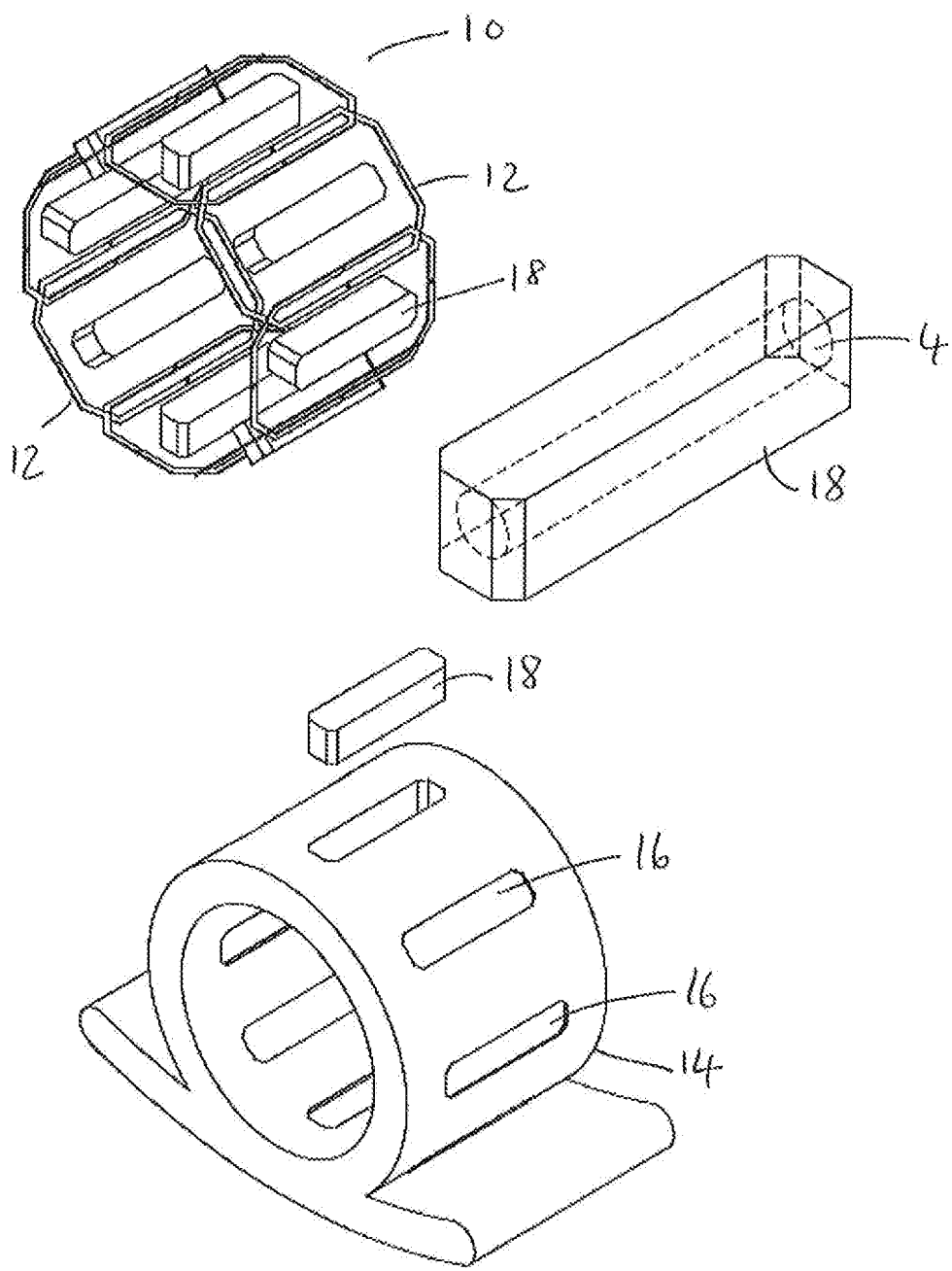
FIG. 3 shows an RF head and neck coil including integrated phantom components.
Figure 4:
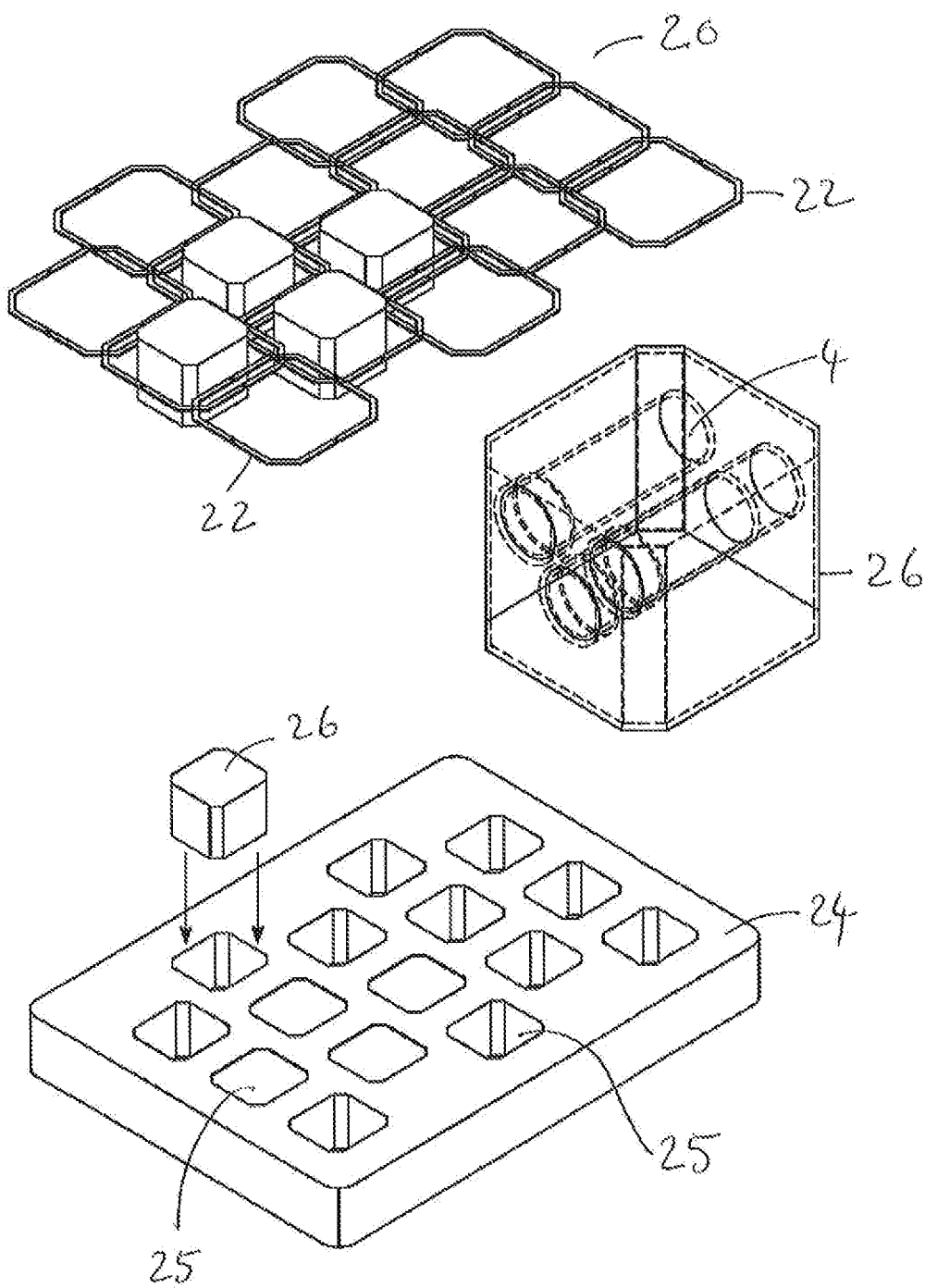
FIG. 4 shows an RF coil array and housing including spaces between the coils, each configured to hold a phantom or a phantom component.

The housing may be shaped in order to be clipped to, or to fit within, the coils of a scanner. To this end, the housing may be sized and shaped such that it can be held in place within gaps present between the coils of the scanner during use. A convenient shape for the housing in this case will be a cuboid, or a shape which is generally cuboid as shown in FIGS. 3 and 4. The structure of the coils will determine the maximum size of the housing, however in some embodiments the cuboid may have a largest dimension of between around 5 cm and around 25 cm (preferably between around 10 cm and around 12 cm). The housing may include an external attachment device (such as a clip or an adhesive strip) for fixing to the coils or a part of the scanner located near to the coils to hold it in place. The fixing mechanism may be removable to allow the phantom to be taken out of the scanner for replacement, maintenance, or in order to be able to adjust the position of the phantom within the scanner for different purposes. The phantom may also be fixed next to the coils (rather than within gaps between the coils) or fixed to a table within the scanner. Even in the case of a cuboid phantom, if the phantom is sufficiently small it can be located next to or on top of a human subject within the scanner without causing discomfort. The minimum size of the phantom will be determined by the resolution of the scanner. The phantom may be modular, as described below.

FIG. 3 shows an example of a coil for extending around the head of the patient (a head or neck coil). The larger coil 10 comprises an array of smaller RF coils 12 located or fixed within a housing 14. The coil housing containing the array includes receptacles or spaces 16 sized to each fit or contain a portion of the phantom. In the example shown, each vial 4 sits within its own separate module 18, and is surrounded by phase change material. Each module is generally cuboid and is shaped for a snug fit in the spaces formed in the phantom housing 14. The spaces may form receptacles including a base to support the modules 18 or may have no base but form a tight fit with the modules 18 such that these remain in place. Some other type of removable attachment mechanism may be used to keep modules 18 in place within the spaces 16 in the housing 14. The larger housing 14 in this embodiment therefore forms the outer housing of the phantom (described above) and contains the phase change material between the outer housing 14 and the vials 4 in separate compartments near to the vials. The outer housing also contains the array of RF coils. Each vial will contain a different concentration of PVP, thickening agent, salt, or another material, as described above in relation to FIGS. 2A and 2B. Of course, more than one vial can be contained within each separate module 18 and some receptacles may be left empty depending on the desired configuration.

The configuration shown in FIG. 3 allows for a great deal of flexibility in terms of which materials are used within the vials as well as the positions of the vials since the separate modules 18 can easily be removed from and placed within any of the spaces 16 available. In the figure, the cuboid housings have cut-aways at the corners which may help ensure a snug fit with the coil housing 14 and, in the embodiments shown, provides a shape which corresponds to that of the RF coil surrounding it.

The same is true in the case of the spinal array shown in FIG. 4. This example is similar to the head and neck coil of FIG. 3 and includes an array 20 of smaller RF coils 22 contained within a housing 24. The housing includes spaces or receptacles 25 sized and shaped to receive smaller modules 26, which contain the vials 4 and the phase change material in the area surrounding the vials. As for the head and neck coil, the spaces may or may not include bases to support modules 26 within the larger housing 24. Each module may again include a single vial, however in the embodiment shown each module houses three separate vials containing different concentrations of the PVP, thickening agent, metallic salt, or other material. Each module may be identical, or may be configured to calibrate different measurements taken with the scanner. One module may include vials containing three solutions of PVP or thickening agent with different concentrations and another module may contain three different metallic salt solutions. Modules may contain more or fewer vials than are shown.

For the head and neck coil and the spinal array, any suitable material (such as any of those described herein) can be used to form the outer housing (14;24), modules (18;26), and vials 4. A solid, rather than flexible, material for the outer housing and the modules may be more suitable in these embodiments in order to ensure that the modules remain in place relative to the outer housing during a scan. Any suitable material can be used as the phase change material and as the material within the vials.

Where a coil is designed to fit around the head, neck, or head and neck of a subject, the phantom may be shaped to fit within the coil and extend around the inner surface. The phantom may extend all of the way around the head or neck of the subject or only a part of the way around, and vials may be similarly located all of the way or part of the way around the head or neck. In general, any shape for the phantom (and any location of the vials within the housing of the phantom) will be suitable provided that it can be located within the imaging volume along with the subject to be imaged.

Because changes in temperature affect the diffusive properties of the liquid or solution within the vials, which may be PVP or paramagnetic metallic salt solution, it is important that the temperature of the solution during the scan is maintained constant and/or is known. To this end, a phase change material is contained within the outer housing of the phantom and surrounds the vials. Phase change materials are able to release large amounts of energy during a change of phase between a liquid and a solid such that no drop in temperature is observed. Depending on the material involved, solidification can last for several tens of minutes so that a constant temperature can be maintained for at least this length of time. The temperature may be monitored during (and/or before and after) the scan to ensure that a constant temperature has been maintained. To achieve this, one or more temperature probes may be placed next to or embedded in the phantom, either within the walls of the vials or housing, or may be positioned to extend into the vials or into the housing (such that the probes may be surrounded by the material within the vials or by the phase change material). A number of these probes may be spaced around the phantom to ensure that the temperature of the phase change material is homogeneous or may extend into or be positioned next to each of the vials to ensure that the material in each vial is also at a constant temperature, and is at the same temperature, to ensure accuracy of the calibration process.

A suitable material to use as a phase change material in a diffusion phantom is thermally cycled ethylene carbonate $((CH_2O)_2CO)$. This material is a transparent crystalline solid at room temperature and has a melting point of 36.3° C. so that its temperature is maintained at 36.3° C. as the material solidifies. Ethylene carbonate is therefore capable of maintaining surrounding material at a temperature similar to that of a patient's skin as it solidifies and can maintain this temperature for over 30 minutes, which is longer than the average scan time. Other phase change materials can replace ethylene carbonate in the phantom. Phase change materials which have a melting point at or around human body temperature are particularly advantageous in terms of comfort for the patient. Phase change materials with a melting point of around 37° C., between 30° C. and 40° C., more preferably between 32° C. and 38° C., or still more preferably between 35° C. and 39° C., may be used to fill the phantom or part of the phantom. An example of a phase change material with a transition temperature of 37 C is PureTemp® 37 which is described at https://www.puretemp-.com/stories/puretemp-37-tds and which is commercially available. The following method used to prepare a phantom for a scan will apply to phantoms including such phase change materials as well as to phantoms containing ethylene carbonate as the phase change material.

Prior to the scan, the phantom may be heated to a temperature of 40 to 50° C. in order to melt the ethylene carbonate or to at or above the melting point of whichever phase change material is used. It is important that the phase change material is fully melted so that when the crystallisation process is initiated the temperature will be homogeneous within the phantom (heating to a temperature above the melting point of the phase change material will help to achieve this). This may be achieved using a bath of warm water into which the phantom is immersed until all of the ethylene carbonate, or other phase change material, has melted. Any method capable of heating the phantom in order to melt the phase change material will be suitable and the heating mechanism may in some embodiments be integrated into the phantom itself or into the scanner. As an example, an electrically powered heating element (such as one or more resistive elements) may be coupled to the phantom on or near to the walls of the outer housing. Current can be passed through the resistive elements prior to the scan in order to heat the phantom and melt the phase change material. The component including the resistive elements may be removed prior to the scan.

The phantom may also incorporate tubes or an additional housing outside of the main housing forming a volume which can be filled with fluid (such as water). This heat transfer fluid can be pumped through to heat the phase change material prior to a scan. If tubes are incorporated, these may run into and within the main housing and into the volume containing the phase change material in embodiments, or may lie outside of the main housing. This heat transfer fluid will have its own thermal control system comprising a pump and a controlled heat source, which may be one or a plurality of resistive heating elements in an embodiment.

Once the ethylene carbonate, or other phase change material, has melted the phantom may be allowed to cool, at which point it will go below its freezing temperature (of 36.3° C. in the case of ethylene carbonate) and will become super-saturated. Once cooled, the phantom can be shaken in order to start the crystallisation process and the latent heat of fusion produced during crystallisation will maintain the phantom at a substantially constant temperature. The scan is then taken of the phantom along with the patient while the crystallisation process is ongoing, such that the liquid within the vials (such as PVP/thickening agent or metallic salt solution) is also kept at a substantially constant temperature. As mentioned, if ethylene carbonate is used, the process of crystallisation will last for at least the average scan time of around 30 minutes. It is not necessary for the material to be pure. For example, ethylene carbonate of 99% purity will still be capable of maintaining a constant temperature for sufficient time for a scan to be taken of the phantom and is readily commercially available. Ethylene carbonate is particularly suitable as a phase change material, however any other phase change material can be used so long as it is able to maintain a stable temperature for long enough for a scan to be completed. A possible alternative is diphenyl ether which has a melting point of around 26° C. Again, although pure diphenyl ether will produce better results, a material having lower purity can be used.

The phantom can be shaken manually or can include a mechanism by which the device can be shaken automatically. A vibrating mechanism, such as a spring-loaded mechanism, may be included in the outer housing of the phantom or may be coupled to or located in the vicinity of the phantom inside the scanner, for example. The skilled person will be aware of the various mechanisms available for vibrating the phantom, or at least the ethylene carbonate therein, without requiring a person to pick the phantom up and physically shake it. Alternatively, an aerosol spray or alternative method can be used to abruptly cool a small volume of the phase change material to create a nucleation point, thus initiating the crystallisation process. A cooling mechanism, such as the spray, can be applied to the external side of the phantom housing to induce a focal point of phase change which can then propagate. One way to achieve this is to use a Ranque-Hilsch vortex tube to separate compressed air into a hot and cold stream and then to direct the jet of cold air at the phantom, either before placing the phantom into the scanner or while the phantom is in-situ.

The phantom may be of a generally elongated and curved shape (as shown). FIG. 2A shows an example of a phantom which is shaped as a curved mat with rounded ends and flat sides. The elongated structure shown in FIG. 2A is easy to produce and is capable of holding the liquid-containing vials close to the body. Ideally, vials which are to be imaged should be as close to the part of the body to be scanned as possible to maximise the accuracy of the calibration. The elongated and curved shape of the phantom enables each vial to be held at an equal distance from, and close to, the body of the patient. The sides do not necessarily need to be flat, although flat sides (6; 8) provide a convenient surface for attachment or location of the ends of the vials 4. If plugs or the like are provided for filling and refilling the vials then the flat surface of the end of the vials in this embodiment is a convenient place to position these.

The particular shape used for the outer housing may depend on the body part which is being imaged and which is adjacent to the phantom during the scan if it is to be located next to or touching the subject within the scanner. In some cases, it is preferable that the phantom is located within the scanner as close to the body part to be imaged as possible. For example, the phantom may be shaped as a hollow semi-circle in order to fit over a patient's head if the MRI scanner is being used to image a patient's brain. Such a shape would also allow the phantom to be directly included in a head coil or a head-and-neck coil, as explained in more detail above. The phantom can also be shaped to fit around the patient's torso, underneath the pelvic area, or underneath various joints of the body (knees, shoulders, ankles etc) for imaging the liver, prostate, and for musculoskeletal applications such as the imaging of joints for inflammatory processes.

Many other applications are also possible and the phantom can be shaped to fit close to any part of the body fairly easily. This can be done either by forming the outer housing of the phantom to fit the shape of a particular body part initially, or to fit the average shape of a particular body part for a number of users (possibly separated by age group or gender), or by forming the outer housing to be flexible enough to conform to any shape. A suitable material to use for the production of a flexible housing is a fluoropolymer elastomer such as FKM or FPM (fluoro rubber). Alternatively, a thin fluoropolymer, such as PTFE or PVDF could be formed into a pouch. Such a flexible polytetrafluoroethylene (PTFE) or polyvinylidene fluoride (PVDF) pouch could also be formed to include an integral filling port formed from solid PTFE or PVDF. The pouch could then be easily filled with the phase change material (such as ethylene carbonate) under a vacuum to prevent the appearance of air bubbles before closing the port.

In an embodiment using a flexible housing, the housing can be formed as a flexible sheet which the patient can lie on or place on top of the body or can even be formed in the shape of an item of clothing such as a hat or vest to ensure that the vials are kept as close to the part of the body to be imaged as possible. Any body part can be imaged in this way with the phantom conforming to the skin closest to the relevant body part. A phantom with flexible housing in the shape of a sheet can generally be placed close to any body part prior during a scan. The vials holding the PVP or other water soluble polymers can also be formed of a flexible material such as PTFE, PVDF, or other plastics. Among others, neoprene-based materials used to form the flexible housing provide particular advantages in that they can help to maintain the phantoms as close to body temperature and as close as possible to the patient's skin, but other type of materials can be used too. Neoprene provides a certain level of insulation, which can help to reduce any heat loss during a scan. The material is also somewhat cushioned, which will increase the comfort of the patient and allows the phantom (and the vials within) to be held close to the patient's body during the scan. The flexibility of the material allows the phantom to conform more closely to the patient's body but may make the relative positions of the vials more difficult to determine.

It may be useful in such a case to incorporate fiducial markers on or adjacent the vials which can be identified in the images in order to fix the positions of the different vials for processing. These may be formed from ink, for example, on the outer or inner surface of the housing of each of the vials. Several markers may be present for each vial in order to track the shape of the vial within the image in a case where a flexible vial housing is employed. Although fiducial markers are described with reference to the flexible housing and may be particularly useful in such an embodiment, these may be used in any phantom, including those employing solid material for the vials and/or outer housing.

In embodiments, a mat incorporating the phantom may be placed on a sliding table such as that shown in FIG. 1A and a patient may be positioned to lie on the mat above the phantom. The phantom could be curved as described above in order to fit comfortably around the base of a patient's back. Comfort is crucial given the long scan times required for diffusion weighted imaging, so that the particular shape of the phantom is particularly important when this type of imaging is used. In embodiments, the phantom may even replace parts of the table on which the subject will lie during the scan. Again, a curved shape could be provided in order to fit the contours of the body (for example the back). The outer housing of the phantom may be formed using a mould taken of a part of the human body to ensure a close fit.

In FIG. 1A, a torso pad is used in order to ensure that the patient does not move too much during the scan. The phantom may, in embodiments, be integrated into this torso pad as shown so that it is strapped onto the patient along with the pad without any additional effort being required on the part of the radiologist administering the scan.

The phantom may also take the place of a cushion placed or fixed inside the scanner. In embodiments, the outer housing of the phantom may be pliable to some extent such that it can mould to the contours of a patient (such as by using the flexible outer housing described above). The phase change material may entirely fill the volume (volume 9 in FIG. 2A) between the vials and the outer housing, or may fill only a part of this volume. In an example, the phase change material fills only an area within the phantom and close to the vials. Each vial can include an outer and inner shell, with the solution contained within the inner shell and the volume between the inner and outer shell being filled with the phase change material. Less of the phase change material is required in such a configuration which may be cheaper overall. In this case the volume between the outer shell of the vial and the outer housing of the phantom may be filled with some type of gel which, if included together with a pliable outer housing, ensures that the phantom is comfortable for a patient to sit or lay on because the phantom will conform, at least to some extent, to the body shape of the patient. Alternatively, the outer housing could be over-moulded with a foam (such as a polyurethane foam) or rubber (such as polyurethane or silicone) in order to provide an outer surface to the phantom which is able to conform at least partly to the body part of the patient being scanned.

The phantom may incorporate a thermometer (such as a fiber optic thermometer) in order to track the temperature of the phantom, and in particular of the solutions within the vials. This will help to ensure that the temperature has indeed remained constant throughout the scan. If this is found not to be the case, some correction may be applied to the value of the measured property to account for this change in temperature over the scan time.

Figure 5:
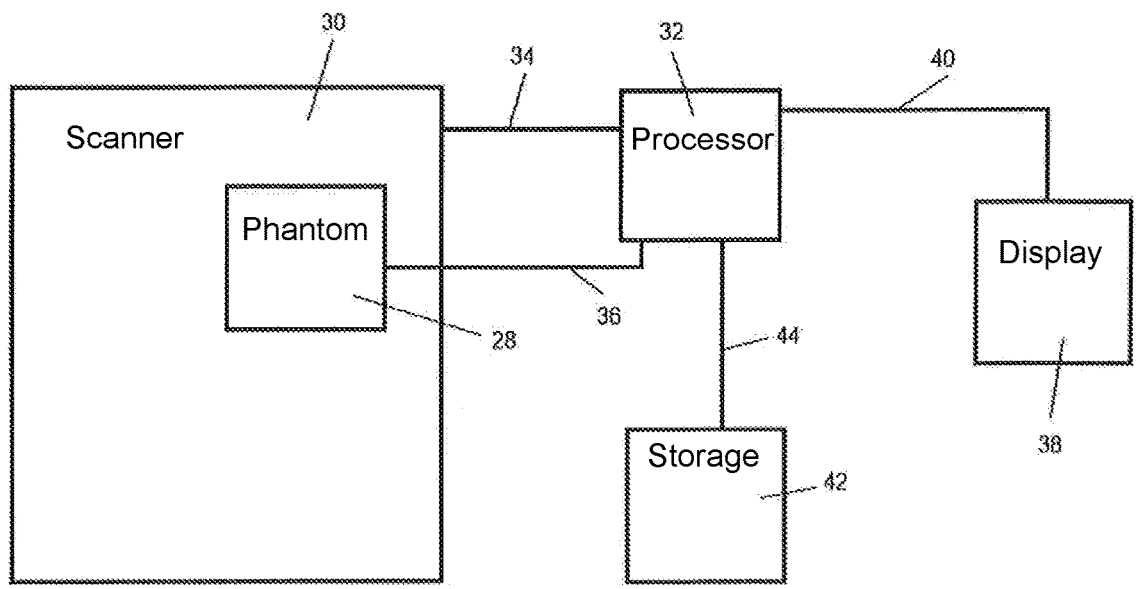
FIG. 5 shows a calibration system including a phantom.

The phantom can form part of a system for use in a scanner. An example of a system including a phantom is shown in FIG. 5. The phantom 28 can be located within a scanner 30, as shown, during image acquisition. Image data from the scanner which will include data relating to the phantom and data relating to the patient is passed to the processor 32 along connection 34. Any other data relating to the status of the phantom, such as temperature data if a thermometer is present, or data relating to crystallisation state of the phase change material, is passed to the processor 32 along connection 36. To this end, the phantom could include an electronics measurement unit. The unit may be located outside of the imaging volume and data sent from the phantom via wireless connection, such as via Bluetooth. Fibre optic cables or regular wires adapted for MR compatibility could be used to transfer data. The processor 32 uses the image data of the phantom and the patient in order to output a properly calibrated image of the patient, or a properly calibrated measurement of a particular property of the imaged body part. Each of the connections in the system may be wireless or wired. The system also comprises a display device 38 for receiving processed/corrected image data via connection 40 and displaying this in a visual format to the user. Storage media 42 can be used to store raw and processed image data, measurements taken using the thermometer, and/or calibration information (such as the form of the inverse function applied to the image data as the correction; see below), which can be passed to storage medium via wired or wireless connection 44 from the processor.

In order to calibrate a diffusion image, a patient sits or lays inside the scanner adjacent the phantom. At this stage, the phantom has been heated, cooled, and then shaken such that the crystallisation process is occurring in the phase change material and the vials therein are being kept at a substantially constant temperature. A minimum of two diffusion weighted images of the patient and the phantom together is taken using the scanner. The ADC is calculated as the rate of change between both diffusion-weighted images acquired with different diffusion-weightings. Each vial will appear on the ADC image and the signal strength will be different for each of the vials since these contain aqueous solutions comprising different concentrations of PVP or thickening agent. A calibration relation (for example a calibration curve) can be produced from the ADC values measured for each of the vials by quantifying the difference between the measured and expected values and this curve can be used to correct measured ADC values in the image of the subject. The expected value is that which would be expected to be measured if the scanner were properly calibrated, since the actual ADC values for the solutions within the vials is known (based on the ADC value of that particular concentration of solution at the temperature of the phase change material during the scan). A similar process will be followed for other imaging methods, which may require the use of different types of solution within the vials, and may not require that more than one image be taken. Other materials which change the apparent diffusion coefficient of a material could be used as well as, or in place of, the PVP. Two main categories of material are possible examples (among others). The first includes additives to water (or another liquid) which modify the ADC, such as PVP or glycerol and the second includes material having a microscopic structure resulting in a change in the ADC. Hydrogels can also be used. A suitable hydrogel for use as the material within the vials (in particular to calibrate diffusion measurements) would be a mixture of water and polyglucan or polyglucans as described above. The concentration of polyglucan in solution could then be varied in order to set the apparent diffusion coefficient. Equal, logarithmic, or other increments in the percentage concentration of polyglucans in solution can be used, as above.

Figure 6:
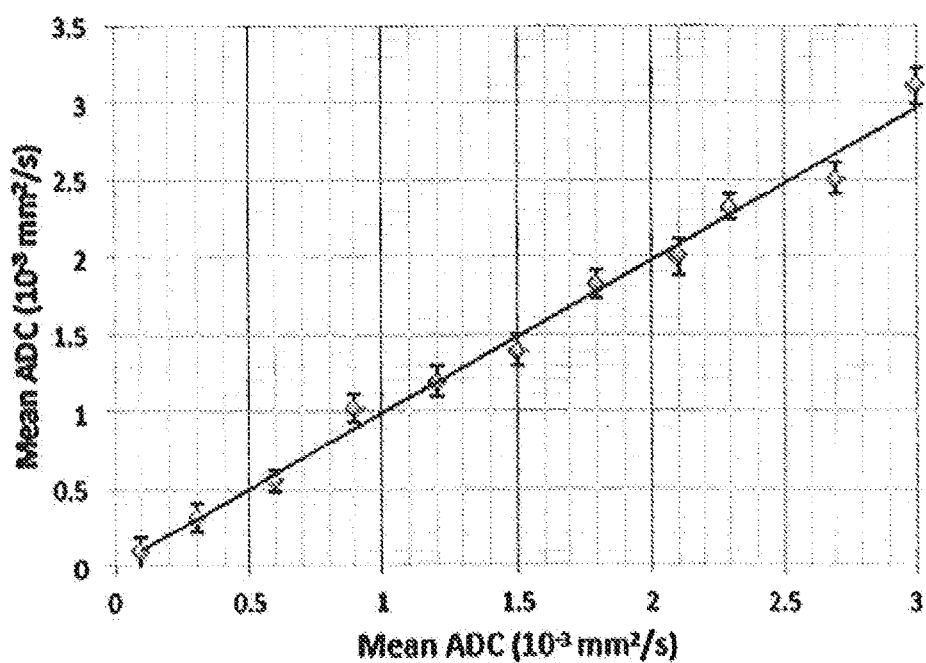
FIG. 6 shows a graph of measured and expected ADC values for each of the vials in a phantom.

FIG. 6 shows a graph plotting ADC values for each of 11 vials containing different concentration solutions of PVP or thickening agent and water. Points show measured values versus known values for each vial. In a perfectly calibrated scanner, these would all lie on the black line shown on the graph (measured=expected). In the example shown, some of the points lie away from the line by an amount greater than the uncertainty in the measurement. A mathematical fit to the set of points can be calculated and an inverse of this function applied to the image data in order to correct for inaccuracies. This process results in a calibrated image of the subject.

The calibration process can also be used to monitor the performance of a scanner year on year since the difference between the measured and expected values of a particular property and the extent and form of the correction which needs to be applied to the image may change over time as the scanner ages or due to specific events. Images and information about the corrections applied each time an image is taken can be sent to storage media and kept for analysis at a later date. Data can be analysed automatically each time an image is taken or can be analysed periodically and an indicator can be provided to alert a user if anomalous results are seen or if the level correction required exceeds a certain threshold, indicating that the scanner's performance has degraded to an unacceptable level. For example, if the sum of the difference between measured and expected values exceeds a predetermined threshold value then an audible or visual signal can be provided.

For each image taken using the scanner, an image of the phantom is taken along with the image of the patient. The above calibration process can be applied either as part of the post processing or during the scan. Because the data used for correction is taken at the same time as the image data itself, because the solution within the vials is kept at an extremely stable temperature by the crystallisation process occurring in the phase change material, and because a number of the vials providing a range of measurements for calibration are located within the scanner as close as possible to the body part to be imaged (due to the contoured shape of the outer housing and the proximity of the vials to the surface of the phantom), the calibration process is very accurate. In the case of DWI, a controlled ADC is achieved which covers a range of values including those representing healthy tissue and severe tumours.

Instead of, or as well as, using a phase change material to maintain the vials at a particular temperature accurate measurements of the temperature of the phantom or of each of the vials can be taken using temperature sensitive sensors. These may comprise optical sensors located within capsules inside or adjacent each of the vials. In an embodiment, a temperature probe insert can be used to monitor temperature before and/or during a scan. Optical sensors are particularly advantageous in the context of MRI scanners because they will not be effected by the strong magnetic fields present inside the scanner during imaging.

Figure 7:
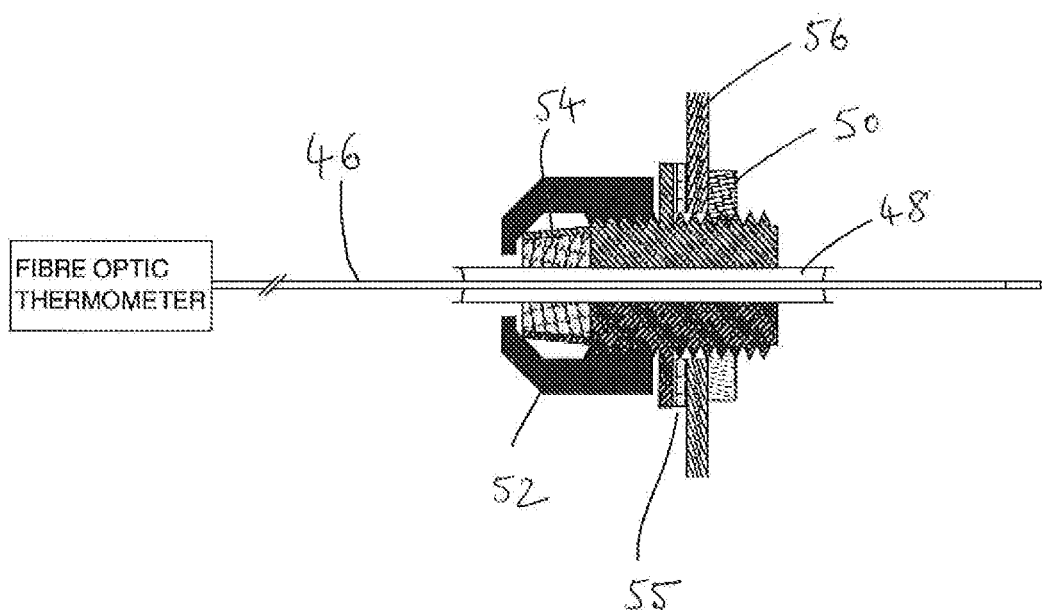
FIG. 7 illustrates an optical temperature probe for use with the phantom or as part of the phantom.

FIG. 7 illustrates a temperature probe comprising a fibre optic cable 46 which sits within a tube 48 (a rigid nylon tube could be used, for example). The tube protects the temperature sensor from being damaged or bent, which may hinder the transport of light along the tube. The fibre optic cable may be potted inside the tube with resin or a similar substance which can provide further protection against unwanted movement of or damage to the cable. Flexible tubing could also be used to protect the optical sensor. In general, the sensor works by delivering light via optical fibre to a material at the end of the fibre, whose optical properties are temperature dependent. This is typically either a thermo-sensitive phorphorescent sensor, or a Gallium Arsenide crystal that has a thermo-sensitive characteristic spectral edge between absorbed and reflected light. The tube is inserted through the wall of the phantom and a gland fixing nut 50 and gland sealing nut 52 help to provide a seal to prevent leakage of the phase change material. The cable and fibre pass through a tube seal 54 partly formed of a screw which passes through a hole formed in the wall of the phantom. The fixing nut 50 is coupled to the screw on one side of the wall of the phantom and the gland sealing nut 52, in some embodiments along with a gland sealing washer 55, are coupled to the screw on the other side (such as the outside) of the phantom wall 56. The gland fixing nut and sealing nut are turned such that they move towards each other along the screw until an effective seal is formed around the hole to prevent leakage from the body of the phantom.

The optic fibre within the tube passes from a fibre optic thermometer coupled to one end for receiving signals in the form of light from the fibre optic cable through the phantom and past portions of the phantom for which it is desired to monitor the temperature. Since it is of particular importance to monitor the temperature at or near to the vials, the fibre optic cable may pass around or past each of the vials in turn, or may even pass through the vials with a similar sealing system as is used at the phantom wall to prevent leakage of fluid into and out of the vessels. The fibre optic cable may pass through the phantom wall twice, once to enter the housing and one to exit.

Figure 8:
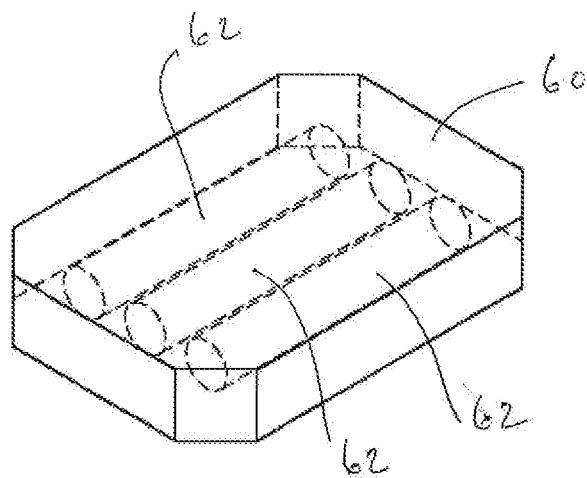
FIG. 8 illustrates a wearable vest into which housing portions containing vessels are incorporated.
Figure 8:
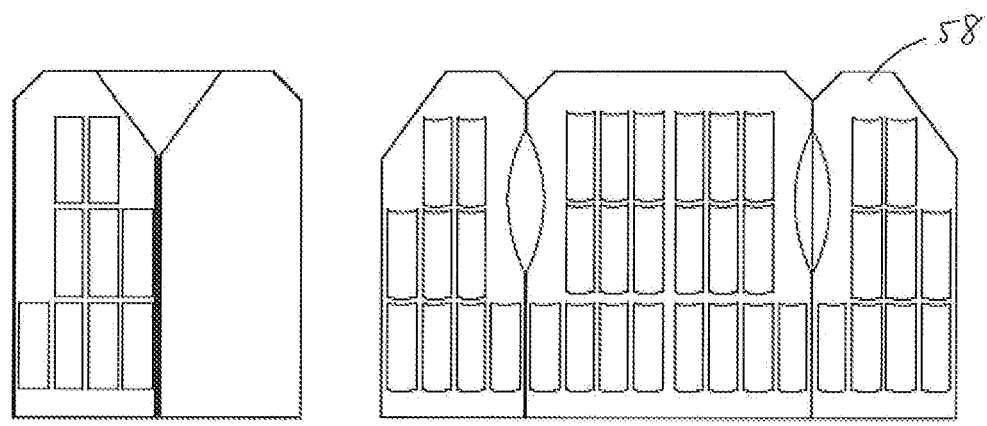
Figure 8:
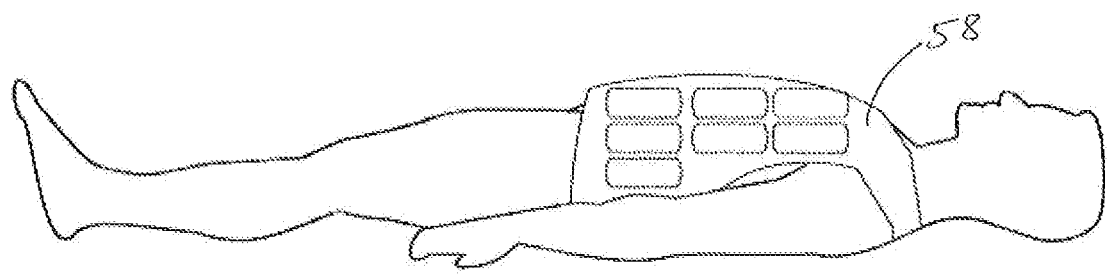

In an embodiment, vessels within their housing may be incorporated into an item of clothing. An example is shown in FIG. 8 which illustrates a vest including a number of pockets in which phantoms can be placed. The housing portion may be sized to correspond to one or more pockets sewn into the vest. The housing shown in the figure is of the solid type described above and includes three vessels with different concentrations of material in each. A vest 58 is formed as shown including a number of pockets. Each of these is adapted to hold a separate housing (such as housing 60 shown in the figure) containing one or more vessels 62. The housing portions may be permanently sewn into the vest or may be removable so that housings can be placed in pockets only near to the area to be imaged prior to a scan. Pockets may be sized to correspond to the size and shape of the housing, may be larger than the housing, or may be sized to contain several separate housings in one pocket. This may make the vest more comfortable for the wearer and means that the vest is adaptable to different situations.

Housings containing a different number of vessels with different solutions therein can also be easily substituted for one another in order to tailor the vest to a particular situation. The same principle of a wearable item including pockets can be adapted to any type of item of clothing, such as trousers, or a hat, for example. Each pocket will be adapted to hold (either permanently or temporarily) one or more housing portions containing phase change material and one or more vessels. In place of pockets, attachment means of any type may be used to fix the housing portions (again either temporarily or permanently) to the item such that when the item is worn the housing or housings will be located near to the area of the body to be imaged and will be held near to this body part to some extent. Fastenings on the item of clothing, such as plastic zips, buttons, or ties may be used to ensure that the item of clothing does not move too much during a scan and that the phantom housings are held as close to the wearer's body as possible.

Embodiments of the present invention have been described with particular reference to the examples illustrated. However, it will be appreciated that variations and modifications may be made to the examples described within the scope of the present invention.

The invention claimed is:

1. A system, comprising:
a phantom for use in a magnetic resonance imaging (MRI) scanner, the phantom comprising:
an outer housing;
a plurality of vessels located within the outer housing, each of the vessels containing a material, wherein the value of at least one property of the material at a particular temperature is different for the material contained within each of the vessels; and
a phase change material between the outer housing and the vessels, wherein the phase change material has a transition temperature or melting point close to body temperature.

2. The system of claim 1, wherein at least a part of an outward facing surface of the outer housing is a concave surface and wherein the vessels are each fixed at an equal distance from the concave surface.

3. The system of claim 1, wherein the outer housing comprises two flat side faces and the vessels extend between and are coupled to the side faces to hold the vessels in position.

4. The system of claim 1, wherein the outer housing is shaped as a cuboid.

5. The system of claim 4, wherein the outer housing has a maximum dimension of 5 cm to 25 cm, such that it can fit and be integrated within RF coils of the MRI scanner.

6. The system of claim 1, wherein the outer housing is configured to be positioned adjacent an inner surface of a head and/or neck coil of the MRI scanner.

7. The system of claim 6, wherein the outer housing is formed as a ring.

8. The system of claim 1, wherein the material within the vessels is a liquid or a polymer dissolved in water, and wherein the concentration of the polymer in solution is different for each of the vessels.

9. The system of claim 8, wherein the liquid within the vessels comprises a metallic salt dissolved in water, and the concentration of the metallic salt is different for each of the vessels and wherein the metallic salt comprises one or more of a compound with paramagnetic ions, Nickel Chloride, Copper Sulphate, Gadolinium, Manganese Chloride, and Iron Oxide.

10. The system of claim 8, wherein the liquid within the vessels comprises one or more of polyvinyl pyrrolidone, a hydrogel comprising water and polyglucan molecules, a mixture of water, and one or more organic oils.

11. The system of claim 1, wherein each of the vessels comprises a vessel inner shell and a vessel outer shell, and wherein the phase change material is contained between the vessel inner shell and the vessel outer shell of each of the vessels.

12. The system of claim 1, wherein the phase change material fills the whole of the space between the vessels and the outer housing.

13. The system of claim 1, comprising an item of clothing including an attachment device, wherein the housing is coupled to the clothing using the attachment device.

14. The system of claim 1, wherein the material within the vessels comprises an injectable MRI contrast agent, and wherein the concentration of the contrast agent in each of the vessels is different.

15. The system of claim 14, wherein the contrast agent is one or more of gadolinium-based, Nickel Chloride, Copper Sulphate, Gadolinium, Manganese Chloride, and Iron Oxide.

16. The system of claim 14, wherein the material within the vessels comprises a gelling agent, and wherein the material within the vessels comprises a compound with paramagnetic ions.

17. The system of claim 16, wherein a ratio of gelling agent to paramagnetic ions is selected such that the material within the vessels matches an intrinsic T1 to T2 ratio of tissue.

18. A method for obtaining calibrated measurements from non-calibrated images using a phantom, the method comprising:
- heating the phantom of claim 1 to melt the phase change material;
- allowing the phase change material to cool;
- disturbing the phase change material to begin a process of crystallisation;
- locating the phantom within the scanner adjacent a subject to be imaged;
- scanning the phantom and the subject simultaneously to produce raw image data while the crystallisation process is ongoing;
- deriving a correction function from values of the property measured from the raw image data of each of the vessels and known values of the property for the material within each of the vessels; and
- applying the correction function to the image data of the subject to produce a calibrated image.

19. The system of claim 1, further comprising a processor coupled to the phantom and to the MRI scanner, the processor configured to:
- receive raw image data of a subject and the phantom;
- derive a correction function from values of the property measured from the raw image data of each of the vessels and known values of the property for the material within each of the vessels; and
- apply the correction function to the image data of the subject to produce a calibrated image.

20. The system of claim 1, further comprising a coil assembly for use in the MRI scanner, the coil assembly comprising a radio frequency coil array and a housing, wherein the housing has one or more spaces between the coils and at least one of the spaces contains the phantom.

21. A method for manufacturing a phantom for use in a magnetic resonance imaging (MRI) scanner, the method comprising:
- filling a plurality of vessels with a material, wherein the value of a property of the material at a particular temperature is different for each of the vessels;
- providing an outer housing surrounding the vessels; and
- providing a phase change material in the volume between the vessels and the outer housing, wherein the phase change material has a transition temperature or melting point close to body temperature.

* * * * *